(12) United States Patent
Masaki (10) Patent No.: US 11,045,074 B2
(45) Date of Patent: Jun. 29, 2021

(54) INSERTION EQUIPMENT, ATTACHMENT TOOL AND DRIVE FORCE TRANSMISSION UNIT

(71) Applicant: OLYMPUS CORPORATION, Tokyo (JP)

(72) Inventor: Yutaka Masaki, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 406 days.

(21) Appl. No.: 16/164,873

(22) Filed: Oct. 19, 2018

(65) Prior Publication Data

US 2019/0053689 A1 Feb. 21, 2019

Related U.S. Application Data

(63) Continuation of application No. PCT/JP2017/011168, filed on Mar. 21, 2017.

(30) Foreign Application Priority Data

Jun. 13, 2016 (JP) .............................. JP2016-117104

(51) Int. Cl.
*A61B 1/00* (2006.01)
*G02B 23/24* (2006.01)

(52) U.S. Cl.
CPC .......... *A61B 1/0016* (2013.01); *A61B 1/0011* (2013.01); *A61B 1/00135* (2013.01); *A61B 1/00154* (2013.01); *G02B 23/24* (2013.01)

(58) Field of Classification Search
None
See application file for complete search history.

(56) References Cited

U.S. PATENT DOCUMENTS

| 5,571,114 A * | 11/1996 | Devanaboyina ... A61B 1/00151 606/1 |
| 2005/0272976 A1* | 12/2005 | Tanaka .................. A61B 1/0016 600/114 |

(Continued)

FOREIGN PATENT DOCUMENTS

| CN | 103889303 A | 6/2014 |
| JP | H03-273878 A | 12/1991 |

(Continued)

OTHER PUBLICATIONS

English translation of International Preliminary Report on Patentability dated Dec. 27, 2018 together with the Written Opinion received in related International Application No. PCT/JP2017/011168.

(Continued)

*Primary Examiner* — Timothy J Neal
(74) *Attorney, Agent, or Firm* — Scully, Scott, Murphy & Presser, P.C.

(57) ABSTRACT

In an insertion equipment, a cover film forming part of an outer periphery surface of an insertion section has flexibility and is formed of a resilient material. In the insertion section, a protrusion protruding to an outer periphery side is covered by the cover film from the outer periphery side, and the protrusion moves around a longitudinal axis with respect to the cover film due to a transmission of a drive force for rotating an attachment tool. A ring member of the attachment tool is attached to the outer periphery side of the cover film in a state that the protrusion is pressed to an inner periphery side by the ring member via the cover film, and is rotatable around the longitudinal axis with respect to the cover film.

13 Claims, 4 Drawing Sheets

(56) References Cited

U.S. PATENT DOCUMENTS

| | | | |
|---|---|---|---|
| 2006/0089533 A1* | 4/2006 | Ziegler | A61B 1/04 600/114 |
| 2006/0270901 A1* | 11/2006 | Bern | A61B 1/0016 600/114 |
| 2008/0009675 A1* | 1/2008 | Kura | A61B 1/00156 600/137 |
| 2008/0183033 A1* | 7/2008 | Bern | A61B 1/0016 600/101 |
| 2010/0210900 A1* | 8/2010 | Allen | A61B 1/31 600/101 |
| 2011/0265275 A1* | 11/2011 | Allen | A61B 1/0016 15/104.05 |
| 2011/0265681 A1* | 11/2011 | Allen | A61B 1/31 104/138.1 |
| 2011/0282150 A1* | 11/2011 | Yamakawa | A61B 1/0016 600/114 |
| 2012/0029281 A1* | 2/2012 | Frassica | A61B 1/00154 600/114 |
| 2012/0029282 A1* | 2/2012 | Yamakawa | A61B 1/0016 600/114 |
| 2012/0029283 A1* | 2/2012 | Yamakawa | G02B 23/2476 600/114 |
| 2012/0046523 A1* | 2/2012 | Yamakawa | A61B 1/00133 600/118 |
| 2012/0053409 A1* | 3/2012 | Yamakawa | A61B 1/0008 600/114 |
| 2012/0053411 A1* | 3/2012 | Yamakawa | A61B 1/00156 600/114 |
| 2012/0165607 A1* | 6/2012 | Ashida | A61B 1/00154 600/114 |
| 2012/0178993 A1* | 7/2012 | Nakamura | A61B 1/00135 600/114 |
| 2012/0184815 A1* | 7/2012 | Yamakawa | A61B 1/00135 600/114 |
| 2012/0184816 A1* | 7/2012 | Ashida | A61B 1/00135 600/114 |
| 2012/0238804 A1* | 9/2012 | Yamakawa | A61B 1/00135 600/101 |
| 2012/0238807 A1* | 9/2012 | Ashida | A61B 1/126 600/109 |
| 2012/0238813 A1* | 9/2012 | Ashida | A61B 1/0125 600/114 |
| 2012/0238814 A1* | 9/2012 | Ashida | A61B 1/00154 600/114 |
| 2012/0238817 A1* | 9/2012 | Ohta | A61B 1/00135 600/115 |
| 2012/0265013 A1* | 10/2012 | Yamakawa | A61B 1/00135 600/114 |
| 2012/0271105 A1* | 10/2012 | Nakamura | A61B 1/00101 600/114 |
| 2012/0271106 A1* | 10/2012 | Yamakawa | A61B 1/00135 600/114 |
| 2012/0271107 A1* | 10/2012 | Yamakawa | A61B 1/01 600/114 |
| 2012/0277530 A1* | 11/2012 | Yamakawa | A61B 1/01 600/114 |
| 2012/0302830 A1* | 11/2012 | Ashida | A61B 1/00154 600/114 |
| 2012/0302831 A1* | 11/2012 | Ashida | A61B 1/00135 600/114 |
| 2013/0006053 A1* | 1/2013 | Yamakawa | A61B 1/0016 600/114 |
| 2013/0035552 A1* | 2/2013 | Moriyama | A61B 1/0016 600/149 |
| 2013/0047391 A1* | 2/2013 | Nakamura | A61B 1/00135 29/270 |
| 2013/0137927 A1* | 5/2013 | Nakamura | A61B 1/00156 600/114 |
| 2013/0144123 A1* | 6/2013 | Nakamura | A61B 1/0016 600/114 |
| 2013/0158349 A1* | 6/2013 | Ashida | A61B 1/0016 600/109 |
| 2013/0158353 A1* | 6/2013 | Nakamura | A61B 1/00135 600/114 |
| 2013/0172679 A1* | 7/2013 | Ashida | A61B 1/00154 600/114 |
| 2013/0197307 A1* | 8/2013 | Ashida | A61B 1/00006 600/114 |
| 2013/0261391 A1* | 10/2013 | Dejima | A61B 1/0016 600/114 |
| 2013/0310646 A1* | 11/2013 | Dejima | A61B 1/0016 600/114 |
| 2014/0012084 A1* | 1/2014 | Naito | A61M 25/0113 600/114 |
| 2014/0012086 A1* | 1/2014 | Yamakawa | A61B 1/00156 600/114 |
| 2014/0046133 A1* | 2/2014 | Nakamura | A61B 1/00135 600/114 |
| 2014/0058203 A1* | 2/2014 | Naito | A61B 1/00158 600/137 |
| 2014/0066713 A1* | 3/2014 | Naito | A61B 1/0669 600/114 |
| 2014/0094654 A1* | 4/2014 | Miyamoto | A61B 1/00156 600/109 |
| 2014/0094657 A1* | 4/2014 | Miyamoto | A61B 1/0016 600/114 |
| 2014/0107419 A1* | 4/2014 | Nakamura | A61B 1/00135 600/114 |
| 2014/0114127 A1* | 4/2014 | Ikeda | A61B 1/0057 600/109 |
| 2014/0135578 A1* | 5/2014 | Naito | G02B 23/2476 600/114 |
| 2014/0194682 A1* | 7/2014 | Umemoto | A61B 1/04 600/103 |
| 2014/0296771 A1* | 10/2014 | Naito | G02B 23/2476 604/19 |
| 2014/0303440 A1* | 10/2014 | Nishiie | A61B 1/00071 600/114 |
| 2014/0316201 A1* | 10/2014 | Umemoto | A61B 1/00006 600/114 |
| 2014/0323805 A1* | 10/2014 | Naito | A61B 1/00135 600/114 |
| 2014/0330079 A1* | 11/2014 | Ishizaki | A61B 1/00071 600/114 |
| 2014/0350461 A1* | 11/2014 | Nishiie | A61B 1/00071 604/95.01 |
| 2015/0105620 A1* | 4/2015 | Oginski | A61B 1/00121 600/112 |
| 2015/0133856 A1* | 5/2015 | Nishiie | A61B 1/00073 604/95.01 |
| 2015/0148607 A1* | 5/2015 | Naito | A61B 1/00135 600/114 |
| 2015/0164303 A1* | 6/2015 | Miyoshi | A61B 1/00135 600/114 |
| 2015/0196191 A1* | 7/2015 | Naito | A61B 1/00156 600/114 |
| 2016/0100743 A1* | 4/2016 | Ailinger | B29C 65/3676 600/114 |
| 2016/0100744 A1* | 4/2016 | Ailinger | A61B 1/0016 600/114 |
| 2016/0135661 A1* | 5/2016 | Ailinger | A61B 1/0016 600/114 |
| 2016/0150945 A1* | 6/2016 | Okamoto | A61B 1/31 600/114 |

FOREIGN PATENT DOCUMENTS

| | | | |
|---|---|---|---|
| JP | 2015-144782 A | | 8/2015 |
| WO | WO 2013/038720 A1 | | 3/2013 |
| WO | WO 2013/147017 A1 | | 10/2013 |

OTHER PUBLICATIONS

Chinese Office Action dated Apr. 30, 2020 in Chinese Patent Application No. 201780026012.3.

(56) References Cited

OTHER PUBLICATIONS

International Search Report dated May 23, 2017 issued in PCT/JP2017/011168.

* cited by examiner

INSERTION EQUIPMENT, ATTACHMENT TOOL AND DRIVE FORCE TRANSMISSION UNIT

CROSS-REFERENCE TO RELATED APPLICATIONS

This is a Continuation Application of PCT Application No. PCT/JP2017/011168, filed Mar. 21, 2017 and based upon and claiming the benefit of priority from prior Japanese Patent Application No. 2016-117104, filed Jun. 13, 2016, the entire contents of which are incorporated herein by reference.

BACKGROUND OF THE INVENTION

1. Field of the Invention

The present invention relates to insertion equipment including an insertion tool and an attachment tool attached to the insertion tool's insertion section. The present invention further relates to an attachment tool provided in the insertion equipment, and a drive force transmission unit configured to transmit a drive force from the insertion section to the attachment tool in the insertion equipment.

2. Description of the Related Art

International Publication No. 2013/038720 discloses a spiral unit (attachment tool) attached to an outer periphery surface of an insertion section of an endoscope (insertion tool). The spiral unit is detachably attached to the insertion section in a state in which it covers the insertion section from an outer periphery side, and includes a spiral fin extending spirally with a longitudinal axis as the center. In the insertion section, a rotor body is attached to a base portion. Also in the insertion section, a cylindrical cover film is attached to the base portion, the cover film covering the rotor body from the outer periphery side. Due to the drive force transmitted in a state in which the spiral unit is attached to the insertion section, the rotor body rotates about the longitudinal axis and presses the spiral unit through the cover film. In this manner, the drive force is transmitted from the rotor body of the insertion section to the spiral unit, causing the spiral unit to rotate about the longitudinal axis. At this point, the spiral unit rotates around the longitudinal axis toward the side where the rotor body rotates.

BRIEF SUMMARY OF THE INVENTION

According to one aspect of the invention, insertion equipment including: an insertion tool which includes an insertion section extending along a longitudinal axis; an attachment tool which is attached to an outer periphery surface of the insertion section, part or all of the attachment tool being configured to rotate around the longitudinal axis due to a drive force transmitted from the insertion section; a cover film which forms part of the outer periphery surface of the insertion section, the cover film having flexibility and being formed of a resilient material; one or more protrusions which protrude to an outer periphery side, and which are covered by the cover film from the outer periphery side in the insertion section, the one or more protrusions being configured to move around the longitudinal axis with respect to the cover film due to a transmission of the drive force for rotating the attachment tool; and a ring member which forms part of an inner periphery surface of the attachment tool, and which is attached to the outer periphery side of the cover film in a state in which the protrusions are pressed to a side toward the longitudinal axis by the ring member via the cover film, the ring member being rotatable around the longitudinal axis with respect to the cover film.

According to one another aspect of the invention, an attachment tool which is used together with an insertion tool, the insertion tool including an insertion section, a cover film, and one or more protrusions, the insertion section extending along a longitudinal axis, the cover film forming part of an outer periphery surface of the insertion section, the cover film having flexibility and being formed of a resilient material, the one or more protrusions protruding to an outer periphery side, the protrusions being covered by the cover film from the outer periphery side in the insertion section, the protrusions being configured to move, due to a transmission of a drive force, around the longitudinal axis with respect to the cover film, the attachment tool being attached to the outer periphery surface of the insertion section, the attachment tool including: a driven section which is configured to rotate around the longitudinal axis due to the drive force transmitted through the insertion section; and a ring member which is coupled to the driven section, and which forms part of an inner periphery surface of the attachment tool, the ring member being attached to the outer periphery side of the cover film in a state in which the protrusions are pressed to an inner periphery side by the ring member via the cover film, the ring member being rotatable around the longitudinal axis with respect to the cover film.

According to one another aspect of the invention, a drive force transmission unit including: a cover film which extends along a central axis, the cover film having flexibility and being formed of a resilient material; one or more protrusions which protrude to an outer periphery side, and which are covered by the cover film from the outer periphery side, the one or more protrusions being configured to move, due to a transmission of a drive force, around the central axis with respect to the cover film; and a ring member which is attached to the outer periphery side of the cover film in a state in which the protrusions are pressed by the ring member via the cover film to an inner periphery side, the ring member being rotatable around the central axis with respect to the cover film.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
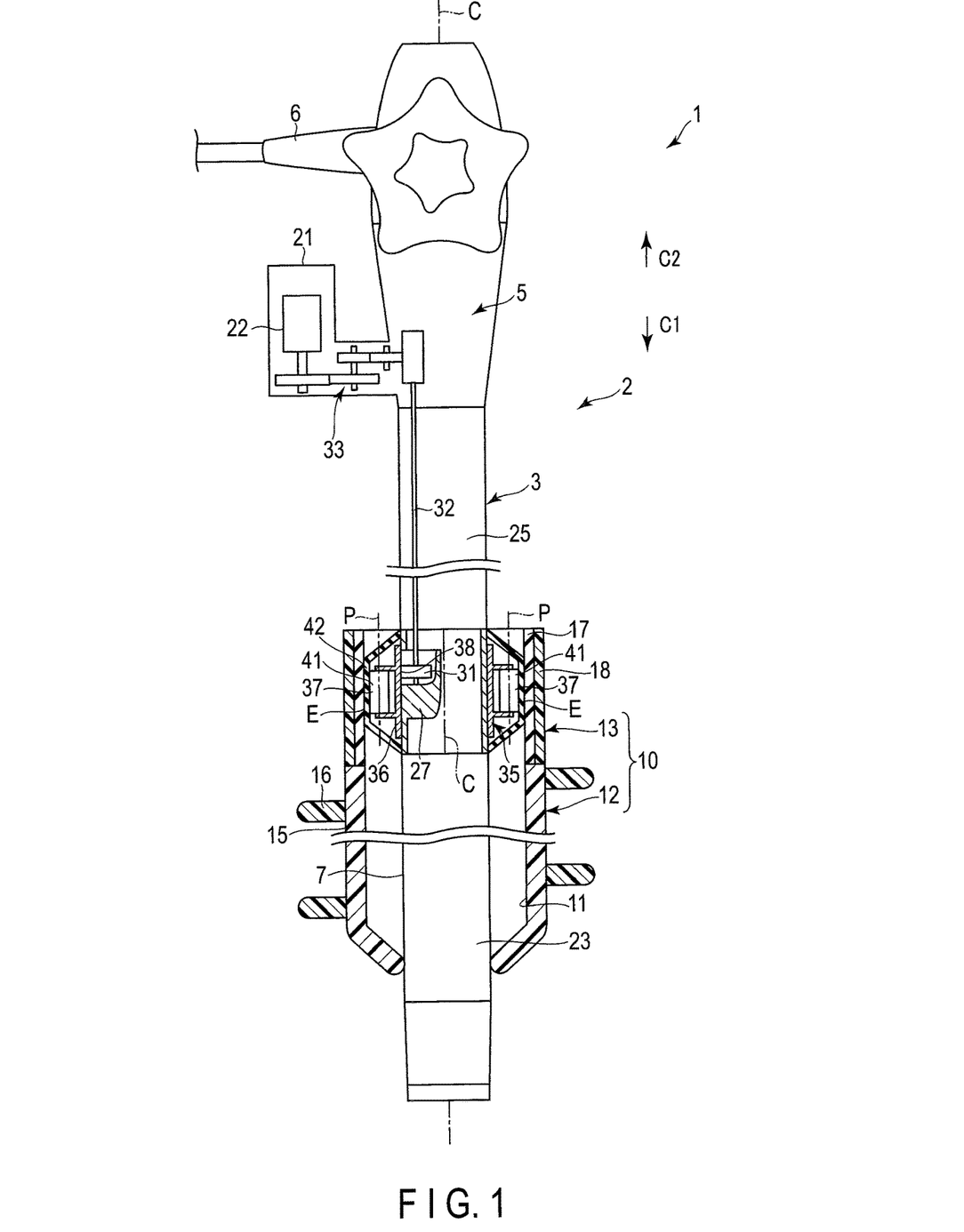
FIG. 1 is a schematic view showing insertion equipment according to a first embodiment.

A first embodiment of the present invention will be described with reference to FIGS. 1 to 5. FIG. 1 is a view showing the insertion equipment 1. As shown in FIG. 1, the insertion equipment 1 includes an endoscope 2 that is an insertion tool, and a spiral unit 10 that is an attachment tool. The endoscope 2 includes an insertion section 3, the insertion section 3 having a longitudinal axis C as a central axis. One side of a direction along the longitudinal axis C (longitudinal axial direction) is a distal side (arrow C1 side in FIG. 1), and a side opposite to the distal side is the proximal side (arrow C2 side in FIG. 1). The insertion section 3 extends along the longitudinal axis C, from the proximal side to the distal side. The insertion section 3 has an outer periphery surface 7. The endoscope 2 includes an operation section 5 provided on the proximal side with respect to the insertion section 3. To the operation section 5, one end of a universal cord 6 is connected.

The insertion equipment 1 is used together with peripheral devices. The peripheral devices include an image processing device (not shown) such as an image processor, a light source device (not shown) such as a lamp, a drive control device (not shown) including an electric power source, a conversion circuit, a processor and a storage medium, an operation input device (not shown) such as a foot switch, and a display device (not shown) such as a monitor. The other end of the universal cord 6 is detachably connected to, for example, the light source device that is one of the peripheral devices.

In the endoscope 2, an imaging cable (not shown) and a light guide (not shown) extend through an interior of the insertion section 3, an interior of the operation section 5, and an interior of the universal cord 6. An imaging element (not shown) such as a CCD is provided inside a distal portion of the insertion section 3. The imaging element takes images of an imaging subject through an observation window (not shown), the observation window being provided on the outer surface of the distal portion of the insertion section 3. Then, via the imaging cable, imaging signals are transmitted to the image processing device (not shown), and then the image processing device performs the image processing. In this manner, the image processing device generates the images of the imaging subject, and then the generated images of the imaging subject is displayed at the display device (not shown). Light emitted from the light source device (not shown) is further guided through the light guide. Then, from an illumination window (not shown) provided on the outer surface of the distal portion of the insertion section 3, the guided light is irradiated on the imaging subject.

The spiral unit 10 is formed into a cylindrical shape. In the insertion equipment 1, the spiral unit (attachment tool) 10 is detachably attached to the outer periphery surface 7 of the insertion section 3 in a state in which the insertion section 3 is inserted through the spiral unit 10. In a state in which the spiral unit 10 is attached to the insertion section 3, the central axis of the spiral unit 10 is approximately coaxial with the longitudinal axis C of the insertion section 3. The spiral unit 10 has an inner periphery surface 11. The spiral unit 10 further includes a driven section (driven object) 12 to be driven, and a connector part (connector) 13 connected to the insertion section 3. The driven section 12 is connected to the distal side of the connector part 13. The driven section 12 includes a cylindrical tube main body 15 extending along the longitudinal axis C (central axis of spiral unit 10), and a spiral fin 16 protruding to the outer periphery side on the outer periphery surface of the tube main body 15. The spiral fin 16 extends spirally about the longitudinal axis C (central axis of the spiral unit 10).

Figure 2:
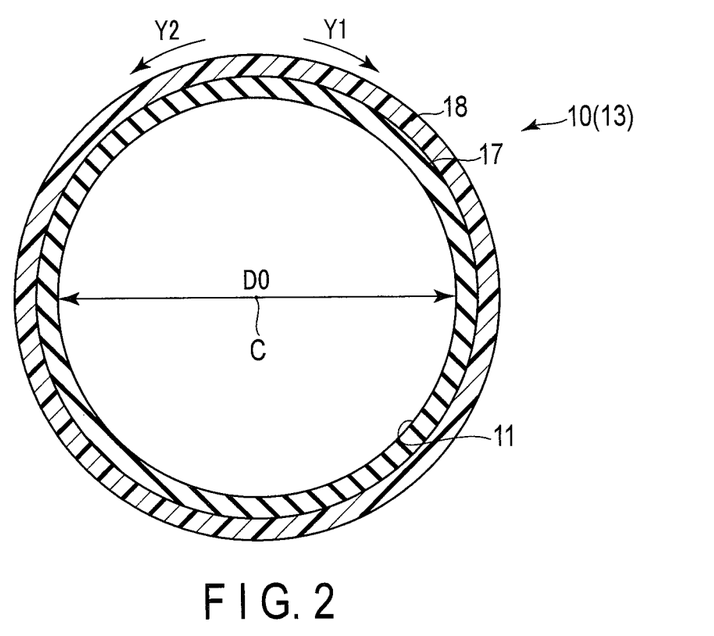
FIG. 2 is a cross-sectional view schematically showing a connector part of a spiral unit in a state where the spiral unit according to the first embodiment is detached from an insertion section, in a cross-section that intersects the central axis of the spiral unit.

The connector part 13 includes a cylindrical ring member 17 forming part of the inner periphery surface 11 of the spiral unit 10, and a cover 18 covering the outer periphery side of the ring member 17. The ring member 17 is formed of an elastomer material or a resilient resin material. Therefore, the ring member 17 is elastically deformable. FIG. 2 is a view showing the connector part 13 of the spiral unit 10 in a state where the spiral unit 10 is detached from the insertion section 3, in a cross-section that intersects (approximately perpendicularly) the central axis (longitudinal axis C) of the spiral unit 10. The ring member 17, as shown in FIG. 2, has an inner diameter D0 in a state in which the spiral unit 10 is detached from the insertion section 3. The ring member 17 further has an inner peripheral length L0. Since the ring member 17 is cylindrical, the inner periphery surface of the ring member 17 is formed into a smooth curved surface. In the embodiment, the entire spiral unit (attachment tool) 10 including the driven section (driven object) 12 and the connector part (connector) 13 is rotatable about the longitudinal axis C.

As shown in FIG. 1, in the endoscope 2, a motor casing 21 is attached to the operation section 5. Inside the motor casing 21, an electric motor 22 is provided as a drive source. To the electric motor 22, one end of an electric wiring (not shown) is connected. The electric wiring is connected to the drive control device (not shown) being one of the peripheral devices, running through the interior of the operation section 5 and through the interior of the universal cord 6. The drive control device controls the supply state of the drive electric power to the electric motor 22 based on the operation input at the operation input device (not shown), and controls the drive state of the electric motor 22. Supplying drive electric power to the electric motor 22 drives the electric motor 22 and generates a drive force causing the spiral unit 10 (driven section 12) to rotate (orbit) about the longitudinal axis C (central axis of spiral unit 10).

The insertion section 3 includes a distal-side flexible tube section 23, and a proximal-side flexible tube section 25 located on the proximal side with respect to the distal-side flexible tube section 23. The proximal end of the proximal-side flexible tube section 25 is connected to the operation section 5. A base portion (stator) 27 formed of a hard material is provided between the distal-side flexible tube section 23 and the proximal-side flexible tube section 25. In other words, the distal-side flexible tube section 23 is connected to the proximal-side flexible tube section 25 via the base portion 27. In a state in which the spiral unit 10 is attached to the insertion section 3, the outer periphery side of the base portion 27 is covered by the connector part 13 (proximal portion of spiral unit 10) of the spiral unit 10, and the spiral unit 10 extends from a region located on the outer periphery side of the base portion 27 toward the distal side. The outer periphery side of the distal-side flexible tube section 23 is then covered by the driven section 12. Note that the number of members forming the base portion (stator) 27 is not limited, and that the base portion 27 may be formed from one member or from a plurality of members.

Figure 3:
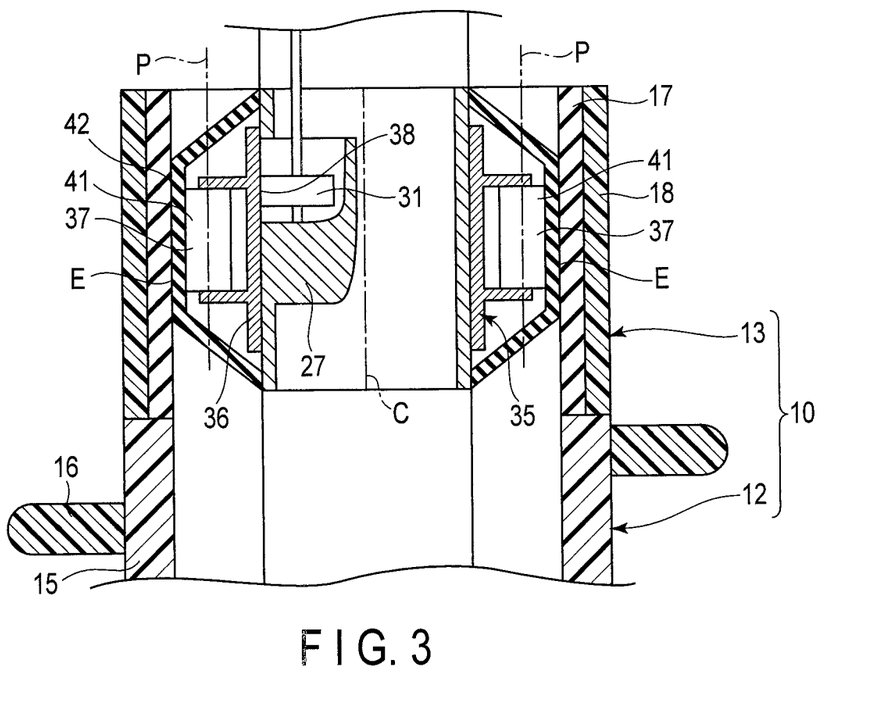
FIG. 3 is a cross-sectional view schematically showing a configuration of a base portion and its vicinity in a state where the spiral unit according to the first embodiment is attached to an outer periphery surface of the insertion section, in a cross-section approximately parallel to a longitudinal axis.
Figure 4:
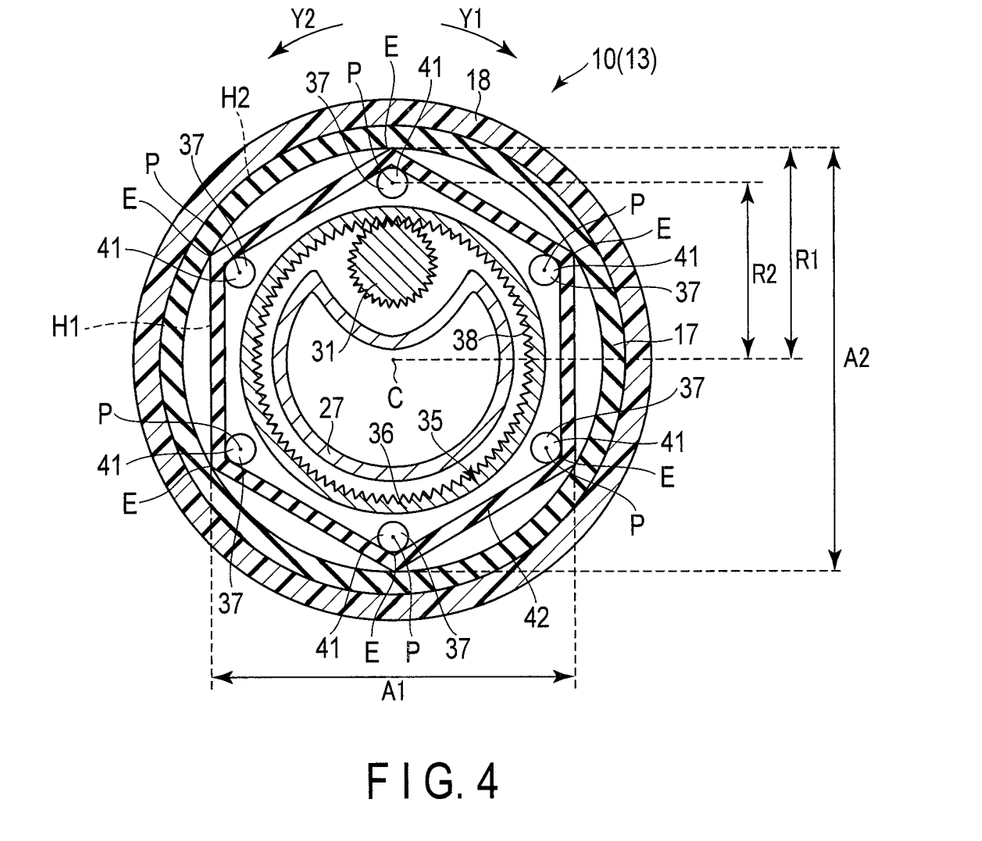
FIG. 4 is a cross-sectional view schematically showing a configuration of the base portion and the vicinity thereof in a state where the spiral unit according to the first embodiment is attached to the outer periphery surface of the insertion section, in a cross-section that intersects the longitudinal axis and that passes through the connector part.

FIGS. 3 and 4 are views showing a configuration of the base portion 27 and its vicinity in a state in which the spiral unit 10 is attached to the outer periphery surface 7 of the insertion section 3. FIG. 3 shows a cross-section approximately parallel to the longitudinal axis C, and FIG. 4 shows a cross-section that intersects (approximately perpendicularly) the longitudinal axis C and that extends through the connector part 13. As shown in FIGS. 1, 3, and 4, a drive gear 31 is disposed inside the insertion section 3. The drive gear 31 is attached to the base portion 27. Inside the proximal-side flexible tube section 25, a drive shaft 32 extends from the proximal side to the distal side. The central axis of the drive shaft 32 is approximately parallel to the longitudinal axis C. The proximal end (one end) of the drive shaft 32 is connected to a gear train 33 inside the operation section 5. The gear train 33 is connected to the electric motor 22 that is the drive source. In other words, the drive shaft 32 is connected to the electric motor 22 via the gear train 33. Further, the distal end of the drive shaft 32 is connected to the drive gear 31. As the electric motor 22 is driven, the drive force is transmitted via the gear train 33 to the drive shaft 32 so as to cause the drive shaft 32 to rotate around the central axis of the drive shaft 32. In this manner, the drive force is transmitted to the drive gear 31 so as to cause the drive gear 31 to rotate.

The insertion section 3 includes a rotor body (rotor) 35 attached to the base portion 27 from the outer periphery side. The rotor body 35 is rotatable with respect to the base portion 27 about the longitudinal axis C. The rotor body 35 includes a rotor base 36 having a cylindrical shape, and (in the embodiment: six) rollers (rotation members) 37 attached to the rotor base 36. On the inner periphery surface of the rotor base 36, an inner peripheral gear 38 is formed. The inner peripheral gear 38 extends across the entire periphery around the longitudinal axis C. The drive gear 31 engages with the inner peripheral gear 38. Therefore, as the drive gear 31 rotates, the drive force is transmitted to the rotor body 35, and the rotor base 36 and the rollers 37 rotate (revolve) together around the longitudinal axis C.

As shown in FIGS. 1, 3 and 4, each of the rollers 37 is rotatable (pivot able) with respect to the rotor base 36 about its corresponding rotation axis (the corresponding one of P). Each of the rollers 37 forms a corresponding protrusion (the corresponding one of 41). Each of the protrusions 41 protrudes to the outer periphery side of the rotor body 35. As the drive force is transmitted to the rotor body 35 and thereby causes the rotor body 35 to rotate around the longitudinal axis C with respect to the base portion 27, each of the protrusions 41 moves around the longitudinal axis C with respect to the base portion 27. The protrusions 41 (rollers 37) are arranged to be spaced apart from each other around the longitudinal axis C.

The insertion section 3 is provided with a cover film 42 that covers, from the outer periphery side, the rotor body 35 including the protrusions 41. The cover film 42 extends along the longitudinal axis C (central axis of the cover film). The cover film is formed of a resilient material, such as a rubber, and has flexibility. Part of the outer periphery surface 7 of the insertion section 3 is formed of the cover film 42. Both the proximal end and the distal end of the cover film 42 are fixed via adhesion or the like to the outer periphery surface of the base portion (stator) 27. This regulates the rotation around the longitudinal axis C (around the central axis of the cover film 42) with respect to the base portion 27 of the cover film (coat) 42. Therefore, as the drive force is transmitted to the rotor body 35, and thereby causes the rotor body 35 to rotate around the longitudinal axis C with respect to the cover film 42, the protrusions 41 move, together with the rotor base 36, around the longitudinal axis C with respect to the cover film 42.

Each of the protrusions 41 presses the cover film 42 from the inner periphery side to the outer periphery side. In this manner, the cover film 42 is elastically deformed by the pressing force from the protrusions 41, and protrudes to the outer periphery side in locations (sites) where the cover film 42 is pressed by the respective protrusions 41. By this, in each of the locations where the cover film 42 is pressed by the protrusions 41, an apex (corresponding one of E) protruding to the outer periphery side is formed on the outer periphery surface of the cover film 42. By connecting, in the cross-section that intersects (approximately perpendicularly) the longitudinal axis C, each of the apexes E in a straight line to its adjacent apex (corresponding one of E) around the longitudinal axis C, a hexagon (polygon) H1 is formed. Since the protrusions 41 in the embodiment are arranged at approximately equal intervals around the longitudinal axis C, the apexes E are also arranged at approximately equal intervals around the longitudinal axis C. The hexagon H1 is therefore a regular hexagon (regular polygon) having the longitudinal axis C as the center. Each of the apexes E forms the vertex of the hexagon H1. Each of the straight lines connecting each of the apexes E to its adjacent apex (corresponding one of E) around the longitudinal axis C forms an edge of the hexagon H1.

Here, in the cross-section that intersects the longitudinal axis C and that passes through the protrusions 41, the outer periphery surface of the cover film 42 has approximately the same shape as the above-mentioned hexagon H1, and the outer peripheral length of the cover film 42 has approximately the same length as a peripheral length L1 of the hexagon H1. The hexagon H1 in the embodiment is a regular hexagon having the longitudinal axis C as the center. Thus, the peripheral length L1 of the hexagon H1 is expressed by Equation (1) to define a radius R1 of a circumcircle H2 of the hexagon H1. Note that the circumcircle H2 is approximately the same as a trajectory circle through which each of the apexes E formed in the cover film 42 runs in the move of the protrusions 41 around the longitudinal axis C, and that the radius R1 is the same as the distance from the longitudinal axis C to each of the apexes E. The peripheral length L1 of the hexagon H1 is expressed by Equation (2) to define both a pitch radius R2 of each of the rollers 37 being the distance from the longitudinal axis C to the axis (corresponding on of P) of each of the rollers 37, and a peripheral length S1 of one roller 37.

$$L1 \approx 6 \cdot R1 \tag{1}$$

$$L1 \approx 6 \cdot R2 + S1 \tag{2}$$

In a state in which the spiral unit (attachment tool) 10 is attached to the outer periphery surface 7 of the insertion section 3, in other words, in a state in which the connector part 13 is connected to the insertion section 3, the ring member 17 is attached to the outer periphery side of the cover film 42. The spiral unit 10 including the ring member 17 is rotatable around the longitudinal axis C with respect to the base portion 27 and the cover film 42. The inner peripheral length L0 of the ring member 17 is longer than the peripheral length L1 of the aforementioned hexagon (regular polygon) H1. Also, the inner peripheral length L0 of the ring member 17 is shorter than the peripheral length L2 of the circumcircle H2 of the hexagon H1. As described above, in the embodiment, an even number of protrusions 41 (apexes E) is provided, and the hexagon H1 is a regular hexagon having the longitudinal axis C as a center. Therefore, since the inner peripheral length L0 is longer than the peripheral length L1 but shorter than the peripheral length L2, the inner diameter D0 of the ring member 17, in a state where the spiral unit 10 is detached from the insertion section 3, is larger than the width across flats A1 of the hexagon H1 but smaller than the width across corner A2 of the hexagon H1.

Since the inner peripheral length L0 is shorter than the peripheral length L2 of the circumcircle H2 (since the inner diameter D0 is smaller than the width across corner A2), the ring member 17 is pressed, in a state in which the ring member 17 is attached to the outer periphery side of the cover film 42, from each of the protrusions 41 to the outer periphery side via the cover film 42, by which the ring member 17 elastically deforms. Therefore, the ring member 17 presses, in a state in which the spiral unit 10 is attached to the insertion section 3, each of the protrusions 41 via the cover film 42 to the inner periphery side (side toward longitudinal axis C). The inner peripheral length L0 is longer than the peripheral length L1 of the hexagon that is approximately the same length as the outer peripheral length of the cover film 42. Thus, in a state where the ring member 17 is attached to the outer periphery side of the cover film 42, the ring member 17 is in contact with the cover film (coat) 42 from the outer periphery side only in the regions where the apexes E (protrusions 41) are located and the vicinities thereof around the longitudinal axis C. In the regions away from any of the apexes E, such as in the regions between each of the apexes E and the adjacent apex (corresponding one of E) around the longitudinal axis C, the ring member 17 is away from the cover film 42 and not in contact with the cover film 42.

Note that the inner peripheral length L0 of the ring member 17 is shorter than the peripheral length L2 of the circumcircle H2 and the ring member 17 is elastically deformed by each of the protrusions 41 pressing the ring member 17, so that, in the regions away from any of the apexes E around the longitudinal axis C, the inner periphery surface of the ring member 17 is located on the inner periphery side with respect to the circumcircle H2 of the hexagon H1. However, since the difference between the inner peripheral length L0 of the ring member 17 and the peripheral length L2 of the circumcircle H2 (i.e., the difference between the inner diameter D0 and the width across corner A2) is very small, the displacement of the inner periphery surface of the ring member 17 with respect to the circumcircle H2 of the hexagon H1 toward the inner periphery side at the locations away from any of the apexes E around the longitudinal axis C is minute. Therefore, in FIG. 4, the displacement of the inner periphery surface of the ring member 17 with respect to the circumcircle H2 of the hexagon H1 at the locations away from any of the apexes E around the longitudinal axis C is not shown, and the inner periphery surface of the ring member 17 is shown as having approximately the same shape as the circumcircle H2.

Figure 5:
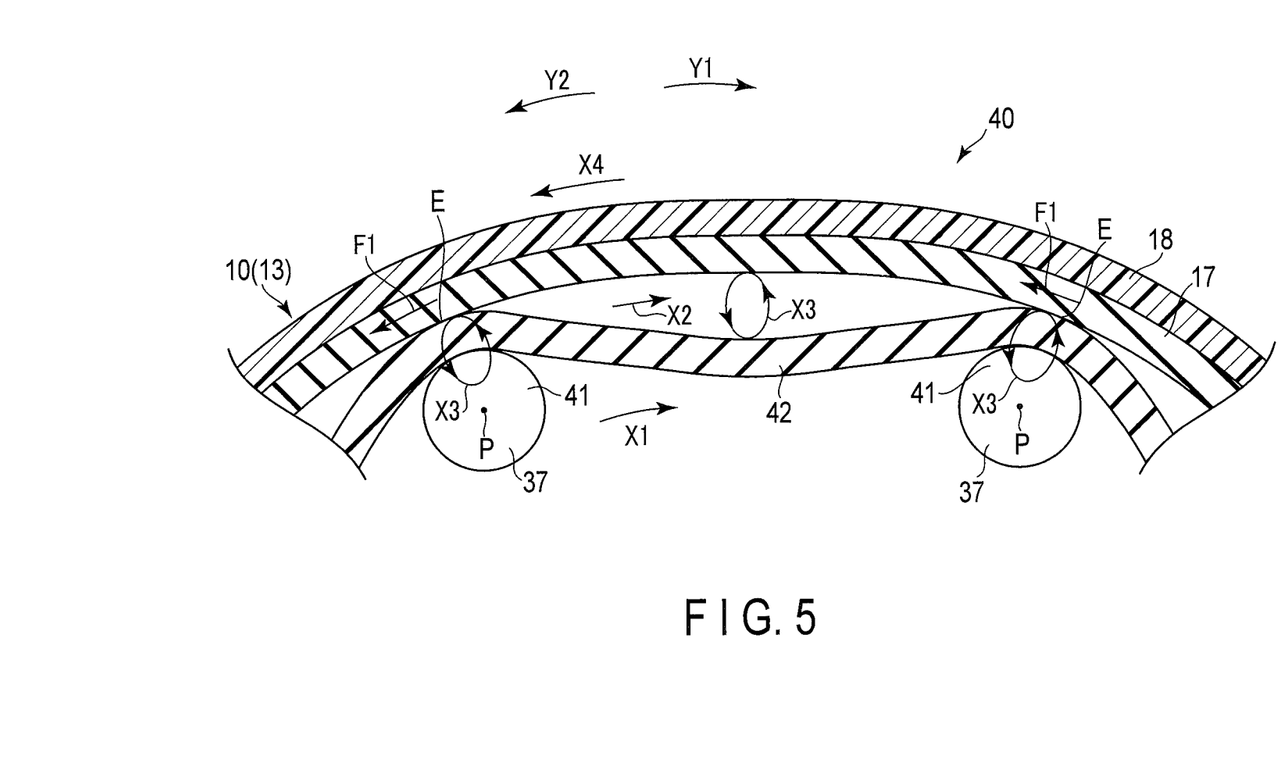
FIG. 5 is a schematic view explaining a configuration for transmitting a drive force for rotating the spiral unit around the longitudinal axis from the protrusion of the insertion section to the connector part of the spiral unit according to the first embodiment.

FIG. 5 is a view explaining the configuration for transmitting the drive force to rotate the spiral unit 10 (driven section 12) around the longitudinal axis C from the protrusions 41 (rotor body 35) to the connector part 13 of the spiral unit 10. In the embodiment, the drive force transmission unit 40 configured to transmit the drive force from the insertion section 3 to the connector part 13 of the spiral unit (attachment tool) 10 is formed of the protrusions 41, the cover film 42, and the ring member 17.

When the rotor body 35 shown in FIGS. 1, 3 and 4 rotates with respect to the cover film 42 toward one side (side of arrow Y1) around the longitudinal axis C, each of the rollers 37 rotates counterclockwise around its own rotation axis P. As shown in FIG. 5, each of the protrusions 41 moves (clockwise in FIG. 5) around the longitudinal axis C toward one side (arrow X1 in FIG. 5). In this manner, the location (site) pressed by each of the protrusions 41 in the cover film 42 also moves to the side where the protrusions 41 move around the longitudinal axis C. In other words, each of the apexes E, which protrude to the outer periphery side in the cover film 42 and at which the ring member 17 is in contact with the cover film 42, moves toward the side where the protrusions 41 move around the longitudinal axis C (side of arrow Y1 in FIG. 5). As the apexes E of the cover film 42 pressed by the protrusions 41 move around the longitudinal axis C, a traveling wave is generated in the cover film (coat) 42. The traveling wave proceeds to the side where the protrusions 41 move around the longitudinal axis C (arrow X2 in FIG. 5).

As the traveling wave moves, each point on the outer periphery surface of the cover film 42 moves elliptically (arrows X3 in FIG. 5). The rotation of the elliptical motion is counter to the travel direction of the protrusions 41 (travel direction of the traveling wave). In FIG. 5, as each of the protrusions 41 moves clockwise around the longitudinal axis C, each point on the outer periphery surface of the cover film 42 moves elliptically counterclockwise. The outer periphery surface of the cover film 42 is in contact with the ring member 17 in the locations (of the apexes E protruding to the outer periphery side in the cover film 42) where pressed by each of the protrusions 41 to the outer periphery side. Therefore, at the apexes E of the cover film 42, due to the elliptical motion of the outer periphery surface of the cover film 42, a force (frictional force) F1 acts on the ring member 17 toward the side opposite to the side where the traveling wave travels, the ring member 17 being in contact from the outer periphery side. Due to the force F1, the spiral unit (attachment tool) 10 including the ring member 17 rotates around the longitudinal axis C to the side opposite to the side where the traveling wave is making the motion (arrow X4 in FIG. 5). Since the traveling wave in FIG. 5 moves clockwise (on the side of arrow Y1) around the longitudinal axis C, the ring member 17 and the driven section 12 rotate counterclockwise (on the side of arrow Y2) around the longitudinal axis C.

Note that the traveling wave is likewise generated by a piezoelectric element in a stator of an ultrasonic motor. Each point on the stator's outer surface makes elliptical motions due to the motion of the traveling wave, and the rotor in contact with the stator's outer surface is caused to rotate toward the side opposite to the side where the traveling wave moves. Therefore, the principle of rotating the spiral unit 10 toward the side opposite to the side where the traveling wave is making the motion by the traveling wave of the embodiment is similar to the principle of rotating the rotor with respect to the stator by the traveling wave generated in the ultrasonic motor's stator.

As described above, each of the protrusions 41 (rollers 37) of the embodiment moves to one side (arrow Y1 side) around the longitudinal axis C, so that a drive force is transmitted to the ring member 17, and the spiral unit 10 including the ring member 17 moves to the side (arrow Y2 side) opposite to the side where the protrusions 41 move around the longitudinal axis C. Similarly, even when each of the protrusions 41 moves to the other side (arrow Y2 side) around the longitudinal axis C, the drive force is transmitted to the ring member 17, and the spiral unit 10 including the ring member 17 moves to the side (arrow Y1 side) opposite to the side where the protrusions 41 move around the longitudinal axis C.

Next, the functions and advantages of the insertion equipment 1 of the embodiment will be described. When observing the lumen using the insertion equipment 1, the spiral unit (attachment tool) 10 is attached to the insertion section 3 of the endoscope (insertion tool) 2, and the insertion section 3 and the spiral unit 10 are inserted into the lumen. By performing an operation input using the operation input device (not shown), the electric motor (drive source) 22 is driven, and, as described above, the drive force is transmitted to the spiral unit 10 via the insertion section 3. As a result, the spiral unit 10 rotates about the longitudinal axis C. When the spiral unit is rotated in a state in which the spiral fin 16 is pressed by the wall of the lumen to the inner periphery side, a propulsion force to the distal side or the proximal side (one of the sides in the direction along the longitudinal axis C) acts upon the insertion section 3 and the spiral unit 10. The propulsion force improves the mobility of the insertion section 3 in the lumen. Since, here, each of the rollers 37 is rotatable about its own rotation axis (corresponding one of P), the friction between the rollers 37 and the cover film (cover tube) 42 is reduced.

In the embodiment, in a state where the protrusions 41 are pressed via the cover film 42 to the inner periphery side, a cylindrical ring member 17 is attached to the outer periphery side of the cover film 42, and the inner periphery surface of the ring member 17 is formed into a smoothly curved surface. In other words, since the drive force in the embodiment is transmitted from the protrusions to the ring member 17 as described above, in the connector part 13 of the spiral unit (attachment tool) 10 including the ring member 17, it is not necessary to provide protrusions (protruding portions) or the like that protrudes to the inner periphery side and is pressed by the protrusions 41. As a result, the configuration of the connector part 13 is simplified, and the labor and cost of manufacturing the spiral unit (attachment tool) 10 are reduced. Since the connector part 13 is not provided with the protrusions protruding to the inner periphery side, the outer diameter of the spiral unit 10 including the connector part 13 can be reduced in diameter. As a result, in the portion of the insertion equipment 1, in which the spiral unit 10 covers the outer periphery side of the insertion section 3, the outer diameter can be reduced.

The inner periphery surface of the ring member 17 being a smooth curved surface is in contact with the apexes E against the cover film 42. Therefore, in a state in which the ring member 17 is attached to the outer periphery side of the cover film 42, the load from the ring member 17 (spiral unit 10) to the cover film 42 is reduced. In this manner, the concentration of stress on the cover film 42 is reduced, and the durability of the cover film 42 is improved.

When the load to the driven section (driven object) 12, for example, the pressing force from the lumen wall or the like to the driven section 12, becomes excessively large, the inner periphery surface (contact surface to the cover film 42) of the ring member 17 slips with respect to the apexes E of the cover film 42 because the inner periphery surface of the ring member 17 being the smooth curved surface is in contact with the cover film (coat) 42. As a result, even when each of the protrusions 41 moves around the longitudinal axis C by the drive force transmitted from the electric motor 22 and the traveling wave is generated in the cover film 42, a drive force from the protrusions 41 is not transmitted through the cover film 42 to the ring member 17 in the drive force transmission unit 40. Therefore, even when the protrusions 41 move around the longitudinal axis C, the spiral unit 10 including the driven section 12 does not rotate around the longitudinal axis C. Therefore, in the embodiment, in a state where an excessive load is applied to the driven section 12, the drive force is prevented from being transmitted to the spiral unit 10, and the spiral unit 10 is prevented from rotating around the longitudinal axis C. In other words, a mechanical torque limit is formed by the drive force transmission unit 40.

In the drive force transmission unit 40, the reduction ratio ε of the rotational speed of the ring member 17 with respect to the motion speed of each of the protrusions 41 (apexes E) is expressed by Equation (3), using the inner peripheral length L0 of the aforementioned ring member 17 and the peripheral length L1 of the hexagon H1 having approximately the same length as the outer peripheral length of the cover film 42.

$$\varepsilon = (L1 - L0)/L0 \qquad (3)$$

Here, the inner peripheral length L0 of the ring member 17 is longer than the peripheral length L1 of the hexagon H1. Therefore, the reduction ratio ε is a negative value. The fact here that the reduction ratio ε in the Equation (3) is a negative value shows that the ring member 17 rotates toward the side opposite to the side where the protrusions 41 (apexes E) move around the longitudinal axis C. Equation (3) further shows that the absolute value of the reduction ratio ε is smaller than 1. Therefore, the rotational speed of the ring member 17 is decelerated with respect to the motion speed of each of the protrusions 41 (apexes E). As the rotation speed of the ring member 17 is decelerated with respect to the motion speed of the protrusions 41, the rotation torque for rotating the ring member 17 is amplified with respect to the rotation torque for moving the protrusions 41. For example, when the reduction ratio ε is −0.9 and the protrusions 41 move around the longitudinal axis C at 50 rpm, the ring member 17 rotates toward the side opposite to the side where the protrusions 41 move around the longitudinal axis C at 45 rpm.

Since the rotational speed of the ring member 17 is decelerated with respect to the motion speed of the protrusion 41 as described above (because the rotary torque of the ring member 17 is amplified from the protrusions 41), it is possible to increase the rotation speed of the rotor body 35 and to reduce the rotary torque of the rotor body 35. In other words, even if the rotary torque of the rotor body 35 is small, the rotary torque of the spiral unit 20 can be increased. Therefore, in the configuration in which the drive force is transmitted from the electric motor 22 to the rotor body 35, it is possible to reduce the speed reduction amount (i.e., the torque amplification amount). In this manner, simplification and miniaturization of the configuration for transmitting the drive force from the electric motor 22 to the rotor body 35 can be realized.

(Modifications)

Note that the number of protrusions 41 (rollers 37) is not limited to the aforementioned embodiments. As long as it is one or more, the number of protrusions 41 is not limited to six. However, the number of protrusions 41 is preferably between 5 and 8.

In the aforementioned embodiment and the like, each of the rollers 37 forms a corresponding one of the protrusions 41, but it is not limited thereto. The rollers 37 thus do not necessarily have to rotate around the rotation axis P. In a modification, rollers (37) are not provided and the rotor body (35) is formed integrally solely from the rotor base (36). Each of the protrusions (41) is formed in the rotor base (36). In the modification, a traveling wave is likewise generated in the cover film (42) by the protrusions (41) moving around the longitudinal axis C. The ring member (17) rotates around the longitudinal axis C toward the side opposite to the side where the protrusions (41) and the traveling wave are making the motion.

Further, in the aforementioned embodiment and the like, the inner peripheral gear 38 is formed in the rotor base 36 of the rotor body 35, but it is not limited thereto. In a modification (not shown), the inner peripheral gear (38) engaging with the drive gear (31) is formed on the inner periphery surface of a cylindrical member, the cylindrical member being a separate member from the rotary body (35). The rotor body (35) includes a rotor base (36) as a supporting member, and one or more rollers (37), and the rollers (37) are in contact with the outer periphery surface of the cylindrical member from the outer periphery side. In the modification, the drive force is transmitted from the drive gear (31) to the cylindrical member, and the cylindrical member rotates around the longitudinal axis C, whereby the drive force is transmitted from the cylindrical member to the rollers (37) of the rotor body (35). As a result, each of the rollers (37) rotates (pivots) about the rotation axis (P) approximately parallel to the longitudinal axis (C) and moves (revolves) around the longitudinal axis (C). In other words, each of the rollers (37) makes a planetary motion. At this point, the rollers (37) rotate toward the side where the cylindrical member rotates around the longitudinal axis (C). As the rollers (37) move around the longitudinal axis (C), the rotor body (35) rotates around the longitudinal axis (C).

According to the modification, each of the rollers (37) also forms a corresponding one of protrusions (41). As described above, each of the protrusions (41) moves around the longitudinal axis C due to the rotation of the rotor body (35). In the modification, a traveling wave is likewise generated in the cover film (42) by the motion of the protrusions (41) around the longitudinal axis C. The ring member (17) then rotates around the longitudinal axis C toward the side opposite to the side where the protrusions (41) and the traveling wave are moving.

In the aforementioned embodiment and the like, the spiral unit (10) has been described as an example of the attachment tool that was attached to the insertion section (3), but the attachment tool is not limited to the spiral unit (10). For example, in the attachment tool according to a modification, a belt member comes into contact with the driven section (12) from the outer periphery side. In this case, when the drive force is transmitted to the ring member (17) and the ring member (17) and the driven section (12) rotate around the longitudinal axis (C), the drive force is transmitted from the driven section (12) to the belt member, and the belt member moves to the proximal side or to the distal side. In other words, according to the modification, as the drive force is transmitted, part of the attachment tool is rotated around the longitudinal axis (C).

In the aforementioned embodiments and the like, the endoscope (2) has been described as an example of the insertion tool, but the insertion tool is not limited to the endoscope (2). For example, the aforementioned configuration may be applied to insertion equipment in which a manipulator is used as the insertion tool.

In the aforementioned embodiment and the like, the insertion tool (2) includes the insertion section (3) extending along the longitudinal axis (C), the attachment tool (10) is attached to the outer periphery surface (7) of the insertion section (3), and, as the drive force is transmitted from the insertion section (3), part or all rotates around the longitudinal axis (C). The cover film (42) forms part of the outer periphery surface (7) of the insertion section (3), has flexibility, and is formed of a resilient material. The insertion section (3) includes one or more protrusions (41) protruding to the outer periphery side, and the protrusions (41) are covered by the cover film (42) from the outer periphery side, and, as the drive force for rotating the attachment tool (10) is transmitted, the protrusions (41) move around the longitudinal axis (C) with respect to the cover film (42). The attachment tool (10) includes the ring member (17) forming part of the inner periphery surface (11), and, in a state in which the protrusions (41) are pressed via the cover film (42) to the inner periphery side, the ring member (17) is attached to the aforementioned outer periphery side of the cover film (42). The ring member (17) is rotatable around the longitudinal axis (C) with respect to the cover film (42).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. Insertion equipment comprising:
   an insertion tool which includes an insertion section extending along a longitudinal axis;
   an attachment tool which is attached to an outer periphery surface of the insertion section, part or all of the attachment tool being configured to rotate around the longitudinal axis due to a drive force transmitted from the insertion section;
   a cover film which forms part of the outer periphery surface of the insertion section, the cover film having flexibility and being formed of a resilient material;
   a rotor body provided in the insertion section and configured to rotate around the longitudinal axis with respect to the cover film due to a transmission of the drive force for rotating the attachment tool, the rotor body including one or more protrusions which protrude further radially relative to other portions of the rotor body toward an outer periphery side of the rotor body, and the rotor body and the one or more protrusions being covered by the cover film from the outer periphery side of the rotor body; and
   a ring member which forms part of an inner periphery surface of the attachment tool, and which is attached to an outer periphery side of the cover film in a state in which the one or more protrusions are pressed to a side toward the longitudinal axis by the ring member via the cover film, the ring member being rotatable around the longitudinal axis with respect to the cover film.

2. The insertion equipment according to claim 1, wherein the ring member is configured to rotate, as the drive force is transmitted due to a motion of the one or more protrusions, toward a direction opposite to a direction where the one or more protrusions move around the longitudinal axis.

3. The insertion equipment according to claim 1, wherein the one or more protrusions comprise a plurality of protrusions, and the plurality of protrusions are circumferentially spaced relative to each other around the longitudinal axis.

4. The insertion equipment according to claim 1, wherein:
each of the one or more protrusions forms, by pressing the cover film toward the outer periphery side of the rotor body, an apex on the outer periphery surface of the cover film; and
in a cross-section that intersects the longitudinal axis, a polygon is formed by connecting each of the apexes with an adjacent apex around the longitudinal axis in a straight line.

5. The insertion equipment according to claim 4, wherein the polygon is a regular polygon having the longitudinal axis as a center.

6. The insertion equipment according to claim 5, wherein an inner peripheral length of the ring member is longer than a peripheral length of the regular polygon, but shorter than a peripheral length of a circumcircle of the regular polygon.

7. The insertion equipment according to claim 1, wherein the ring member is formed of an elastomeric material or a resin material that has elasticity.

8. The insertion equipment according to claim 1, wherein:
the rotor body includes a rotor base rotating around the longitudinal axis together with the one or more protrusions due to the transmission of the drive force, and one or more rotation members attached to the rotor base; and
each of the rotation members forms a corresponding one of the one or more protrusions, and is rotatable with respect to the rotor base having a rotation axis parallel to the longitudinal axis as a center.

9. An attachment tool which is used together with an insertion tool, the insertion tool including an insertion section, a cover film, and a rotor body, the insertion section extending along a longitudinal axis, the cover film forming part of an outer periphery surface of the insertion section, the cover film having flexibility and being formed of a resilient material, the rotor body being provided in the insertion section and being configured to rotate, due to a transmission of a drive force, around the longitudinal axis with respect to the cover film, the rotor body including one or more protrusions protruding further radially relative to other portions of the rotor body toward an outer periphery side of the rotor body, the rotor body and the one or more protrusions being covered by the cover film from the outer periphery side of the rotor body, the attachment tool being attached to the outer periphery surface of the insertion section,
the attachment tool comprising:
a driven section which is configured to rotate around the longitudinal axis due to the drive force transmitted through the insertion section; and
a ring member which is coupled to the driven section, and which forms part of an inner periphery surface of the attachment tool, the ring member being attached to an outer periphery side of the cover film in a state in which the one or more protrusions are pressed to a side toward the longitudinal axis by the ring member via the cover film, the ring member being rotatable around the longitudinal axis with respect to the cover film.

10. The attachment tool according to claim 9, wherein the ring member is configured to rotate, as the drive force is transmitted due to a motion of the one or more protrusions around the longitudinal axis, toward a direction opposite to a direction where the one or more protrusions move around the longitudinal axis.

11. The attachment tool according to claim 9, wherein the ring member is formed of an elastomeric material or a resin material that has elasticity.

12. A drive force transmission unit comprising:
a cover film which extends along a central axis, the cover film having flexibility and being formed of a resilient material;
a rotor body configured to rotate, due to a transmission of a drive force, around the central axis with respect to the cover film, the rotor body including one or more protrusions which protrude further radially relative to other portions of the rotor body toward an outer periphery side of the rotor body, and the rotor body and the one or more protrusions being covered by the cover film from the outer periphery side of the rotor body; and
a ring member which is attached to an outer periphery side of the cover film in a state in which the one or more protrusions are pressed by the ring member via the cover film to a side toward the central axis, the ring member being rotatable around the central axis with respect to the cover film.

13. The drive force transmission unit according to claim 12, wherein the ring member is configured to rotate, as the drive force is transmitted due to a motion of the one or more protrusions around the central axis, toward a direction opposite to a direction where the one or more protrusions move around the central axis.

* * * * *